United States Patent [19]

Boyen

[11] 4,010,744
[45] Mar. 8, 1977

[54] FOOT-NECK HARNESS DEVICE

[76] Inventor: Steven G. Boyen, 3875 Wilshire Blvd., Los Angeles, Calif. 90005

[22] Filed: Mar. 11, 1976

[21] Appl. No.: 665,880

[52] U.S. Cl. ................................................ 128/75
[51] Int. Cl.² ........................................ A61H 1/02
[58] Field of Search ........... 128/75, 78, 84 R, 84 C, 128/80 R, 80 G, 31; 272/79 R, 80

[56] References Cited
UNITED STATES PATENTS

| 324,498 | 8/1885 | Surbaugh | 128/31 |
| 359,903 | 3/1887 | Stephens | 128/31 |
| 807,908 | 12/1905 | Bradstreet | 128/80 G X |
| 2,377,940 | 6/1945 | Hughes | 128/75 X |
| 3,295,517 | 1/1967 | Stevens | 128/78 X |
| 3,556,090 | 1/1971 | Viel | 128/75 |

Primary Examiner—John D. Yasko
Attorney, Agent, or Firm—John Joseph Hall

[57] ABSTRACT

A harness device having a pair of heel-foot slings with heel straps attached by leg straps to rings connected to shoulder-chest straps for maintaining flexion of a person's hips and knees and traction of the low neck-upper back area.

2 Claims, 3 Drawing Figures

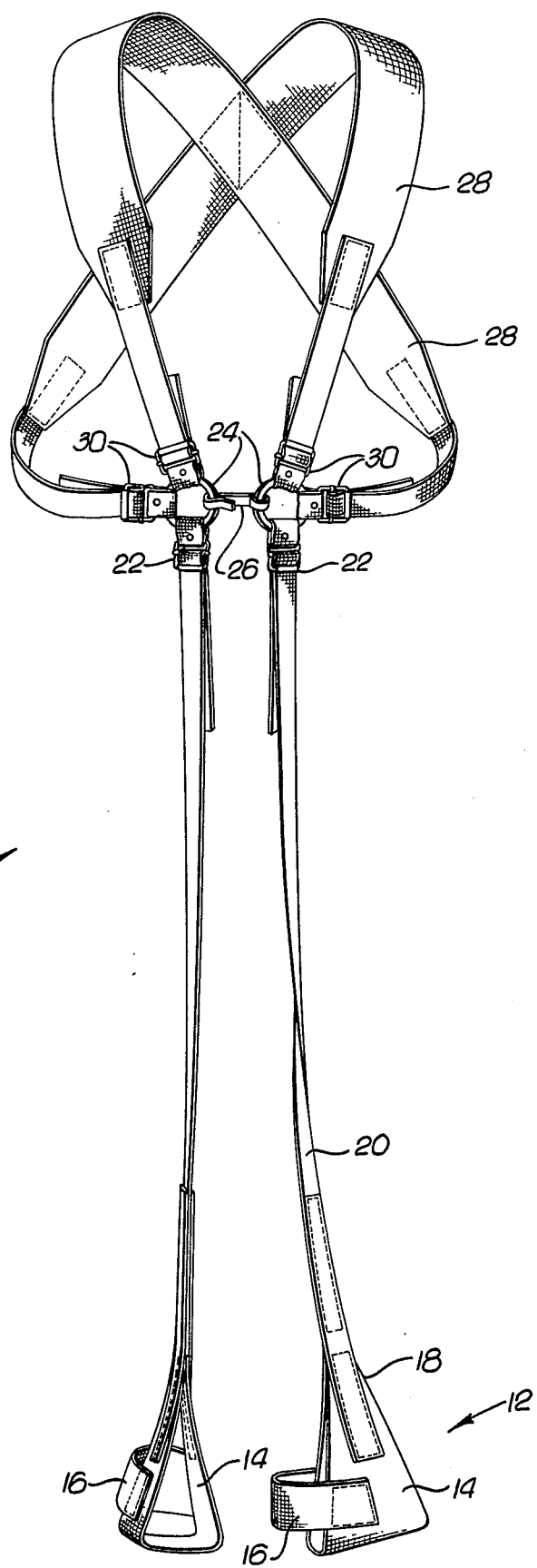

FOOT-NECK HARNESS DEVICE

SUMMARY OF THE INVENTION

The vast majority of low back ailments are due to injuries, acute and chronic, to the disc of the spine. The injuries to the discs are due to the activity of everyday living or working, or the acute trauma of an accident. Conventional treatment of acute and chronic low back ailments usually consists of bed rest, a variety of corsets and braces, and pelvic traction. All these measures have the common purpose of widening the disc spaces. My invention also provides widening of the disc spaces not only better than the conventional methods, but with less expense and discomfort, and can be done at home, and also while a patient is asleep.

My invention is designed to achieve results comparable to traction without the need of traction weights and hospital placement and supervision of a patient. Also, my invention permits the patient to sleep or recline on one side rather than on his back, thereby improving the traction results.

The invention comprises a harness with a pair of heel-foot slings having heel straps, one for each foot of the patient. Each of the slings is connected to a leg strap. Each of the leg straps in turn is connected to a ring member which has shoulder-chest straps attached to it for securing the harness on a person.

The length of leg straps and shoulder-chest straps is adjustable so that they can be pulled taut to maintain a person's hips and knees in a flexed position, thereby maintaining hip flexion and exerting downward traction at a person's low neck-upper back area, whereby a flattening of the lordotic curve of the lumbar spine with a widening of the disc spaces will tend to take place. Such traction is equivalent to that of conventional traction in a hospital for low back ailments, besides permitting a patient to sleep or recline on one side rather than on his back only.

It is, therefore, an object of this invention to provide means for maintaining a person's hips and knees in a flexed position and traction of the low neck-upper back area.

Another object is to provide means for maintaining hip flexion and traction on a person's low neck-upper back area while a person is sleeping or reclining in a horizontal, left or right lateral position.

A further object of this invention is to provide means for maintaining hip flexion and traction on a person's low neck-upper back area which a person can receive outside a hospital.

A still further object of this invention is to provide means for maintaining hip flexion and traction on a person's low neck-upper back area which a person can use by himself, and which can be achieved while a person is sleeping.

A yet further object of this invention is to provide means for maintaining hip flexion and traction on a person's low neck-upper back area which is relatively easy and inexpensive to use by a lay person.

These and other objects will be more readily understood by reference to the following description and accompanying drawings, in which FIG. 1 is a perspective view of an embodiment of the invention in place on a person.

FIG. 3 is a perspective view of an embodiment of the invention in a longitudinal extended position.

Figure 1:
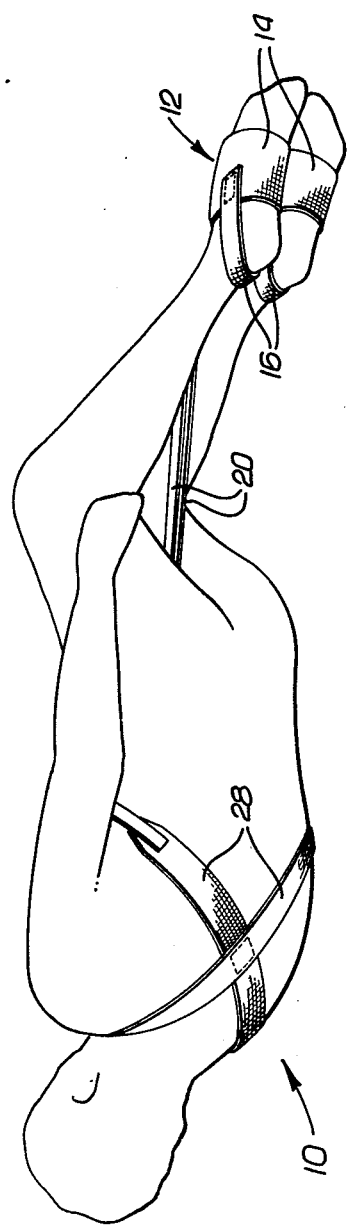

The foot-neck harness 10 has a heel-foot sling assembly 12, including a foot sling 14 and a heel strap 16, one for each foot of a person. The foot sling 14 and heel strap 16 are preferably made of any suitable material which is soft, smooth and sturdy.

The heel strap 16 may be connected by any suitable means to the rear edge of slings 14 or may be formed integrally with slings 14.

The triangular sides of slings 14 are preferable but the form is not critical. The tops 18 of each of slings 14 are connected by sewing or other suitable means to each other and also to the lower end of a leg strap 20. The upper end of each leg strap 20 is secured to an adjustable buckle 22. Each of buckles 22 are connected pivotally to a ring member 24. One of the ring members 24 has a hook device 26 attached to it for hooking both rings 24 together, preferably about an inch apart.

Shouler-chest straps 28 are adjustably connected at each of their ends to adjustable buckles 30. One set of buckles 30 are each pivotally connected to one ring member 24 and the other set of buckles 30 are connected to the other ring member 24.

The shoulder-chest straps 28 cross over each other at their mid-portion as shown in FIGS. 1 and 3, and are preferably connected together at that point by any suitable means. The mid-portion of shoulder-chest straps 28 may be widened for improving a person's comfort when wearing the harness 10.

Figure 2:
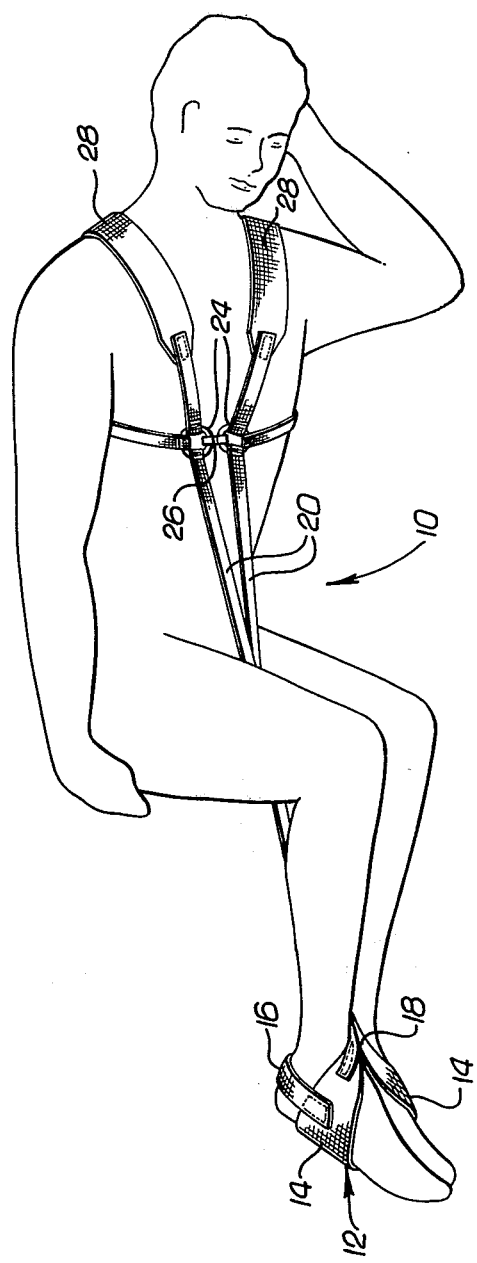
FIG. 2 is a perspective view showing an embodiment of the invention in place on a person from the front.

In operation, the harness is placed on a person as indicated in FIGS. 1 and 2 with his feet in slings 12. The leg straps 20 are pulled taut and buckles 22 are adjusted to maintain the person's hips and knees in a flexed position. The shoulder-chest straps 28 are also pulled taut. Hook 26 is attached to the other ring member 24 so that both rings 24 are joined together about one inch apart preferably, and buckles 30 are adjusted to maintain the flexed position of the person's hips and knees.

In this manner, the harness 10 will maintain a position of flexion of a person's hips and knees while the person is sleeping or reclining in a horizontal, left or right lateral position. While keeping the hips and knees in flexion, the harness 10 will exert some downward traction at the low neck-upper back area, thereby tending to flatten the lordotic curve of the lumbar spine with a widening of the intervertebral disc spaces. Maintaining this position of flexion is desirable and beneficial in a variety of chronic and acute low back ailments. Upon a person's arising out of bed, the foot slings 12 are easily slipped off, with the harness 10 remaining in place. The patient can then walk around at home and, upon returning to bed, may then slip on the foot slings 12. To put on or take off the entire harness 10 takes only seconds if the patient is so disposed.

Although I have described my invention in detail with reference to the accompanying drawings illustrating a preferred embodiment of my invention, it is understood that numerous changes in the details of construction and arrangement of parts may be made without departing from the spirit and scope of the invention as hereinafter claimed.

I claim:

1. A harness device for maintaining flexion of a person's hips and knees while reclining in a horizontal lateral position, comprising:

sling means for securing a person's feet and including heel strap means, shoulder-chest strap members having adjustable lengths and attached to ring members, said ring members being connected to each other in close proximity and located in a position corresponding to the approximate center of said person's chest, strap members with adjustable lengths, said strap members connecting said sling means to said ring members, and formed to extend in close proximity to each other and longitudinally between said person's legs from said sling means to said ring members while said person is reclining in a horizontal lateral position, whereby traction is produced and maintained on said person's low neck-upper back area when said harness device is pulled taut on said person.

2. A harness device according to claim 1 in which one of said ring members has hook means for joining said ring members together.

* * * * *